United States Patent [19]

Düscher

[11] 4,220,636
[45] Sep. 2, 1980

[54] STABILIZED SUPPOSITORIES CONTAINING ERGO-ALKALOIDS

[75] Inventor: Renate-Else Düscher, Solingen, Fed. Rep. of Germany

[73] Assignee: Deutsche Gesellschaft fuer Unwelt-Schutz e. V., Solingen, Fed. Rep. of Germany

[21] Appl. No.: 958,503

[22] Filed: Nov. 7, 1978

[51] Int. Cl.² .......................... A61J 3/08; A61K 31/48
[52] U.S. Cl. ...................................... 424/14; 424/175; 424/261
[58] Field of Search .......................... 424/175, 14, 261

[56] References Cited

U.S. PATENT DOCUMENTS 3,149,035  9/1964  Riegelman .......................... 424/175
3,526,698  9/1970  Polli et al. ............................ 424/175
4,092,410  5/1978  Ogata et al. ......................... 424/175

OTHER PUBLICATIONS

Chemical Abstracts, vol. 81 (1974), p. 68510u.
Chemical Abstracts, vol. 68 (1968), p. 62652b.

Primary Examiner—V. D. Turner

[57] ABSTRACT

The present invention relates to stabilized suppositories containing ergo-alkaloids and/or their derivatives, characterized in that $SO_2$-releasing substances are added in a finely dispersed state to the suppositories in amounts of 0.2 to 5 mg per suppository. The invention provides a safe route for the treatment of migraine not affected by nausea, which often occurs with the condition.

3 Claims, No Drawings

STABILIZED SUPPOSITORIES CONTAINING ERGO-ALKALOIDS

Combination preparations containing ergo-alkaloids, in particular ergotamine, are very often used to treat migraine and the accompanying headaches.

In general orally administered preparations, i.e. pills, capsules, tablets, drops, etc., are employed for this purpose.

However, the symptoms of nausea often associated with migrain contra-indicate the use of oral medication, and the preparations therefore have to be administered parenterally or rectally.

The latter of these two modes of application is preferred since the patient can administer it himself, which is particularly important as migraine attacks often occur suddenly and are prolonged.

Ergotamine tartrate and other ergo-alkaloids are generally the main active ingredient in migraine suppositories on account of their specific action on the blood vessels of the brain.

However, in the case of suppositories containing ergotamine tartrate—we are considering here the commercial preparations—the insufficient stability of the ergotamine is a serious problem.

Ergo-alkaloids and their derivatives are decomposed by light, water, oxygen, heat and other unknown factors into decomposition products, some of which are still unidentified. However, it can be established from the decreasing van-Urk titre that the lysergic acid fraction in the alkaloid is always involved in the decomposition. However, there are also isomerisation reactions that result in inactive isomers.

The decomposition phenomena are manifested in the ergotamine-containing suppositories by a colouration effect, which starts at light beige and continues to dark brown. The decomposition of the alkaloid can be detected by the decreasing van-Urk titre even before the first visible colouration. As far as is known at present, the decomposition products of ergotamine are inactive.

Attempts have been made to stabilise preparations containing ergoalkaloids by adding $SO_2$—releasing compounds, such as e.g. sodium disulphite, sodium bisulphite or disodium sulphite. Such sulphur-containing compounds have already been used and investigated over a fairly long period as stabilisers, e.g. for adrenalin and adrenalin derivatives in solutions for injection, in vitamins such as ascorbic acid and aneurine, and also in antibiotics such as Neomycin, Tetracyclin, Chlortetracyclin, Oxytetracyclin, and in alkaloids and alkaloid derivatives such as sparteine, apomorphine, atropine, eserine, etc.

Sodium bisulphite and sodium disulphite have already been used in ergotamine and other ergo-alkaloids, but preferably in liquid preparations such as Secale extracts and particularly also in solutions for injection.

The results were however of limited use and insufficient, without deterioration data, for commercial products.

B. Siegfried and R. Schneider (Pharm. Helv. Acta 28, 169–177 (1953) state on pages 175–176 in their article on "die Stabilisation von Extractum Secalis cornuti fluidum Ph.H.V." (the stabilisation of extract of Secalis cornuti fluidum Ph.H.V.), that the addition of 1 0/00 sodium hydrogen sulphite has in practice been found to be ineffective for stabilising ergot alkaloids.

I. N. Kurchneko and F. A. Konev (C.A. 64, 7973 (1966) even report that sodium disulphite in solutions for injection accelerates the decomposition of ergotamine.

There are numerous other reports on attempts to stabilise ergotamine or other ergo-alkaloids with various other substances, e.g. ascorbic acid, thiourea, cysteine, etc. The success of such attempts was however limited, and in no case were they sufficiently satisfactory to enable a commercial preparation corresponding to the present-day stability requirements to be produced on this basis. Some of these stabilisers are also suspect for toxicological reasons.

There is no published material at all on the stability of suppositories containing ergotamine or ergo-alkaloids.

An investigation of various ergotamine tartrate-containing suppositories that are sold in pharmacies ahd chemists' shops in the Federal Republic of Germany showed that these were either visibly discoloured or contained coloured substances (colourants) that masked such a discolouration. It was found analytically that the ergotamine content was in some cases 30–40% below the stated value.

The object of the invention is thus to provide stabilised suppositories containing ergo-alkaloids.

According to the state of the art outlined above, it would not have been expected that $SO_2$—releasing substances would stabilise suppositories. It was however surprisingly found that suppositories containing ergo-alkaloids, in particular ergotamine, can be rendered stable for years by adding $SO_2$—releasing compounds.

By the term "ergo-alkaloids" are meant genuine alkaloids derived from Secale cornutum such as ergotamine, ergocristine and ergometrine, as well as their dihydro derivatives such as dihydroergotamine, which are preferably employed in the form of their salts.

$SO_2$—releasing compounds that can be used are the alkali, alkaline earth and magnesium salts of sulphurous acid and pyrosulphuric acid, as well as their addition products with aldehydes and ketones, such as e.g. sodium acetone bisulphite. Preferably compounds are sodium disulphite ($Na_2S_2O_5$), sodium bisulphite, and disodium sulphite.

Suppositories in this context also include rectal capsules which contain, within a gelatin casing, a soft, fatty mass in which the active ingredients and the stabiliser are incorporated.

Suppositories stabilised in such a way can obviously, contain only active ingredients that are not incompatible with the stabilisers.

With regard to toxicity, there are no grounds for fear in the case of suppositories containing $SO_2$-releasing compounds, and thus for example eye-drops containing 0.3% sodium disulphite ($Na_2S_2O_5$) are sold commercially in the Federal Republic of Germany. According to D. Hauschild (Pharmacologie und Grundlagen der Toxicologie, 4th Edition; Berlin 1973, page 375), the addition of sodium sulphite or sodium hyposulphite or acetone bisulphite is harmless even in solutions for ampoules.

An example and comparison with unstabilised suppositories:

The suppositories of the stabilised formulation contained the following components:

| | |
|---|---|
| 1. Ergotamine tartrate USP XVIII | 0.325 mg |

-continued

| | | |
|---|---|---|
| 2. | Sodium disulphite DAB 7 DDR | 0.500 mg |
| 3. | Butylhydroxyanisole Ph.Helv.VI | 2.000 mg |
| 4. | Aneurine nitrate DAB 7 | 5.000 mg |
| 5. | caffeine DAB 7 | 60.000 mg |
| 6. | Dimethylaminophenyldimethylpyrazolone DAB 7 | 100.000 mg |
| 7. | Suppository base | 1190.000 mg |

The unstabilised formulation contains the same components, but no sodium disulphite.

The suppository base was a mixture of the triglycerides of natural saturated vegetable fatty acids having a chain length of $C_{12}$ to $C_{18}$.

Butylhydroxyanisole is a known antioxidant for fats, oils, etc, and is a mixture of 2-butyl-4-hydroxyanisol and 3-butyl-4-hydroxyanisole. This fat antioxidant has no stabilising effect on ergotamine tartrate.

The sodium disulphite and likewise the ergotamine tartrate must be very finely ground (grain size < 0.1 mm).

The suppositories of both formulations were produced in a conventional manner and stored at room temperature in commercially available, hermetically sealed foils. The ergotamine in these suppositories was determined immediately after production and after fairly prolonged intervals of time during storage, in the following manner:

Three parallel series of determinations are carried out.

4 suppositories are accurately weighted ($=P_x$) and dissolved as far as possible in 40 ml of petroleum spirit (R 79) in a separating funnel, and then mechanically shaken for 15 minutes with 50.00 ml of a 5% aqueous tartaric acid solution.

10.00 ml of van-Urk reagent (1) are then added dropwise from a burette to 5.00 ml of the aqueous phase in a beaker, while stirring with a magnetic stirrer. After about 30 minutes the extinction of the solution is measured against a blank solution of 5.00 ml of 5% aqueous tartaric acid solution and 10.00 ml of van-Urk reagent in 1 cm cells at 548 nm ($=E_x$):

Calculation:

$$\frac{\bar{x} \cdot E_x \cdot 5.69}{P_x} = \text{mg ergotamine tartrate/suppository}$$

$E_x$ = Extinction of the sample solution
$P_x$ = Weighed sample (in mg)
$\bar{x}$ = Average suppository weight (in mg)

The differences in stability between the suppositories stabilised according to the example and the unstabilised suppositories, which were prepared as described in the example but without the addition of sodium disulphite, are shown in the accompanying drawing.

In the case of suppositories that are stabilised with such a chemically active substance as $SO_2$, there is still the danger that the ergotamine will be decomposed by the stabiliser with the formation of colourless decomposition products, especially when it is recalled that such substances in some cases give a positive van-Urk reaction, but they can be distinguished from ergotamine by their Rf-value in thin layer chromatography.

For this reason the stabilised suppositories were investigated by the following method for these "foreign alkaloids."

10.00 ml of the suppository extract (corresponding to 0.25 mg of ergotamine tartrate) made up to 50.0 ml with 5% aqueous tartaric acid solution are made alkaline with approx. 1 ml of 6 N ammonia solution (R 38) and extracted by shaking with 5.0 ml of chloroform (R 129). The chloroform phase is dried with a small amount of anhydrous sodium sulphate (RR 337), filtered in a pointed, graduated centrifuge glass (15 ml, subdivided in 0.2 ml divisions), and the sodium sulphate is then carefully washed with approx. 2.5 ml of chloroform.

The chloroform is carefully concentrated by evaporation to approx. 0.2 ml in a boiling water bath. This liquid remainder is drawn up in a small syringe provided with a long needle and "spotted" on a thin layer chromatography plate coated with silica gel (thin layer chromatography plate, 5 cm × 20 cm, Merck 5724).

The solution is developed with a mixture of chloroform (R 129) and methanol (R 268) (15:1 parts by volume) up to a running height of approx. 140 mm.

The plate is dried in a current of warm air and is then sprayed with the van-Urk reagent. The ergotamine spot was found at Rf=approx. 0.35. The foreign alkaloids were recognisable only as weak spots of Rf approx. 0.11, Rf approx. 0.46 and Rf approx. 0.69.

A parallel test was carried out with pure ergotamine tartrate USP XVIII, whose thin layer chromatogram was practically the same.

(1) van-Urk reagent
0.8 ml of a 5% aqueous ferric chloride solution is added to a cooled mixture of 280 ml of distilled water and 520 ml of concentrated sulphuric acid (R 425). 1.60 mg of p-dimethylaminobenzaldehyde are dissolved in this mixture while stirring, and the resultant solution is stored in a cold place away from light. It can be kept for about 4 weeks in a cold cupboard at +4° C.

The references in brackets (R . . . ) given after the reagents mentioned herein refer to the DAB 7 Reagent Catalogue.

Since this method provides only an estimate of the foreign alkaloids and does not enable normally unexpected decomposition products or decomposition products that give a negative van-Urk reaction to be detected, a thin layer chromatography plate with a fluorescence indicator was prepared from the same solution, which enables the unchanged ergotamine to be determined quantitatively with a scanner (densitometer).

It was surprisingly found that the ergotamine in the suppositories prepared according to the example had not changed in the slightest after storage for 33 months at room temperature.

I claim:

1. A stabilised suppository containing at least one member of the group consisting of alkaloids derived from Secale cornutum and their dihydro derivatives, in a medically effective amount for the treatment of migraine headaches, characterised in that at least one $SO_2$-releasing substance selected from the group consisting of alkali, alkaline earth and magnesium salts of sulphurous acid and pyrosulphuric acid and the addition products of said salts with aldehydes and ketones is added in a finely dispersed state to the suppository in an amount of 0.2 to 5 mg per suppository.

2. A suppository according to claim 1, wherein sodium disulphite ($Na_2S_2O_5$) or sodium bisulphite are used as the $SO_2$-releasing substance.

3. A suppository according to claim 1, which contains ergotamine or a salt thereof as said alkaloid.

* * * * *